(12) United States Patent
Ward et al.

(10) Patent No.: US 10,524,849 B2
(45) Date of Patent: Jan. 7, 2020

(54) SYSTEM AND METHOD FOR CATHETER-BASED PLASMA COAGULATION

(71) Applicant: COVIDIEN LP, Mansfield, MA (US)

(72) Inventors: Arlen K. Ward, Englewood, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 256 days.

(21) Appl. No.: 15/645,522

(22) Filed: Jul. 10, 2017

(65) Prior Publication Data

US 2018/0036059 A1 Feb. 8, 2018

Related U.S. Application Data

(60) Provisional application No. 62/370,035, filed on Aug. 2, 2016.

(51) Int. Cl.
*A61B 18/04* (2006.01)
*A61B 18/00* (2006.01)

(52) U.S. Cl.
CPC .. *A61B 18/042* (2013.01); *A61B 2018/00589* (2013.01); *A61B 2018/00642* (2013.01);
(Continued)

(58) Field of Classification Search
CPC . A61B 18/042; A61B 18/148; A61B 18/1492; A61B 18/14; A61B 18/1206; A61B 18/1482; A61B 18/1402; A61B 18/1815; A61B 18/12; A61B 18/1233; A61B 18/1477; A61B 18/04; A61B 18/18; A61L 2/0011; A61F 9/00736; H05H 1/24; H05H 1/46
See application file for complete search history.

(56) References Cited

U.S. PATENT DOCUMENTS 3,434,476 A 3/1969 Shaw et al.
3,492,074 A 1/1970 Rendina
(Continued)

FOREIGN PATENT DOCUMENTS

CN 2391565 Y 8/2000
DE 3710489 A1 11/1987
(Continued)

OTHER PUBLICATIONS

Ward et al., "A Significant New Contribution to Radical Head and Neck Surgery"; Arch Otolaryngology, Head and Neck Surg., vol. 115 pp. 921-923 (Aug. 1989).
(Continued)

*Primary Examiner* — Manuel A Mendez

(57) ABSTRACT

A plasma instrument includes an elongated body defining a lumen therethrough, the lumen being in fluid communication with an ionizable media source; and a plasma applicator coupled to a distal portion of the elongated body. The plasma applicator includes: an active electrode configured to couple to an active terminal of a generator; and a corona electrode configured to couple to a return terminal of a generator. The plasma instrument also includes a switching element coupled to the corona electrode, the switching element configured to control at least one of resistivity or connectivity of the corona electrode to a generator.

17 Claims, 4 Drawing Sheets

(52) U.S. Cl.
CPC .............. *A61B 2018/00827* (2013.01); *A61B 2018/00892* (2013.01); *A61B 2018/00988* (2013.01)

(56) References Cited

U.S. PATENT DOCUMENTS

| | | | |
|---|---|---|---|
| 3,687,832 A | 8/1972 | Fydelor et al. | |
| 3,838,242 A * | 9/1974 | Goucher | A61B 18/042 128/908 |
| 4,188,426 A | 2/1980 | Auerbach | |
| 4,517,495 A | 5/1985 | Piepmeier | |
| 4,699,082 A | 10/1987 | Hakim | |
| 4,781,175 A | 11/1988 | McGreevy et al. | |
| 4,837,484 A | 6/1989 | Eliasson et al. | |
| 4,855,563 A | 8/1989 | Beresnev et al. | |
| 5,013,959 A | 5/1991 | Kogelschatz | |
| 5,024,617 A | 6/1991 | Karpiel | |
| 5,041,110 A | 8/1991 | Fleenor | |
| 5,194,740 A | 3/1993 | Kogelschatz et al. | |
| 5,466,424 A | 11/1995 | Kusano et al. | |
| 5,776,255 A | 7/1998 | Asaba et al. | |
| 5,780,862 A | 7/1998 | Siess | |
| 5,866,871 A | 2/1999 | Birx | |
| 5,869,832 A | 2/1999 | Wang et al. | |
| 5,945,790 A | 8/1999 | Schaefer | |
| 6,153,852 A | 11/2000 | Blutke et al. | |
| 6,159,208 A | 12/2000 | Hovda et al. | |
| 6,172,324 B1 | 1/2001 | Birx | |
| 6,203,542 B1 | 3/2001 | Ellsberry et al. | |
| 6,264,650 B1 | 7/2001 | Hovda et al. | |
| 6,376,972 B1 | 4/2002 | Tarasenko et al. | |
| 6,407,513 B1 | 6/2002 | Vollkommer et al. | |
| 6,432,103 B1 | 8/2002 | Ellsberry et al. | |
| 6,464,695 B2 | 10/2002 | Hovda et al. | |
| 6,468,270 B1 | 10/2002 | Hovda et al. | |
| 6,475,217 B1 * | 11/2002 | Platt | A61B 18/042 606/40 |
| 6,488,825 B1 | 12/2002 | Hilliard | |
| 6,501,079 B1 | 12/2002 | Furuya | |
| 6,544,261 B2 | 4/2003 | Ellsberry et al. | |
| 6,602,248 B1 | 8/2003 | Sharps et al. | |
| 6,772,012 B2 | 8/2004 | Ricart et al. | |
| 6,837,884 B2 | 1/2005 | Woloszko | |
| 7,004,941 B2 | 2/2006 | Tvinnereim et al. | |
| 7,070,596 B1 | 7/2006 | Woloszko et al. | |
| 7,090,672 B2 | 8/2006 | Underwood et al. | |
| 7,094,215 B2 | 8/2006 | Davison et al. | |
| 7,179,255 B2 | 2/2007 | Lettice et al. | |
| 7,270,659 B2 | 9/2007 | Ricart et al. | |
| 7,318,823 B2 | 1/2008 | Sharps et al. | |
| 7,331,956 B2 | 2/2008 | Hovda et al. | |
| RE40,156 E | 3/2008 | Sharps et al. | |
| 7,387,625 B2 | 6/2008 | Hovda et al. | |
| 7,393,351 B2 | 7/2008 | Woloszko et al. | |
| 7,491,200 B2 | 2/2009 | Underwood | |
| 7,628,787 B2 * | 12/2009 | Sartor | A61B 18/042 606/41 |
| 7,708,733 B2 | 5/2010 | Sanders et al. | |
| 8,157,795 B2 | 4/2012 | Sartor et al. | |
| 9,117,636 B2 | 8/2015 | Koo et al. | |
| 9,269,544 B2 | 2/2016 | Koo et al. | |
| 9,532,826 B2 | 1/2017 | Sartor | |
| 2003/0038912 A1 | 2/2003 | Broer et al. | |
| 2003/0069576 A1 | 4/2003 | Tanrisever | |
| 2003/0088245 A1 | 5/2003 | Woloszko et al. | |
| 2003/0093073 A1 | 5/2003 | Platt | |
| 2003/0158545 A1 | 8/2003 | Hovda et al. | |
| 2005/0004634 A1 | 1/2005 | Ricart et al. | |
| 2005/0010205 A1 | 1/2005 | Hovda et al. | |
| 2005/0119650 A1 | 6/2005 | Sanders et al. | |
| 2005/0149012 A1 | 7/2005 | Penny et al. | |
| 2005/0153159 A1 | 7/2005 | Sugiyama et al. | |
| 2005/0234439 A1 | 10/2005 | Underwood | |
| 2005/0261754 A1 | 11/2005 | Woloszko | |
| 2006/0091109 A1 | 5/2006 | Partlo et al. | |
| 2006/0200122 A1 | 9/2006 | Sartor et al. | |
| 2007/0010809 A1 | 1/2007 | Hovda et al. | |
| 2007/0027440 A1 | 2/2007 | Altshuler et al. | |
| 2007/0029500 A1 | 2/2007 | Coulombe et al. | |
| 2007/0045561 A1 | 3/2007 | Cooper | |
| 2007/0106288 A1 | 5/2007 | Woloszko et al. | |
| 2008/0122368 A1 | 5/2008 | Saito et al. | |
| 2009/0024155 A1 | 1/2009 | Lee-Sepsick et al. | |
| 2010/0125267 A1 | 5/2010 | Lee et al. | |
| 2010/0130973 A1 | 5/2010 | Choi et al. | |
| 2010/0204690 A1 | 8/2010 | Bigley et al. | |
| 2011/0139751 A1 | 6/2011 | Koo et al. | |
| 2011/0301414 A1 * | 12/2011 | Hotto | A61B 1/00009 600/114 |
| 2012/0289954 A1 | 11/2012 | Lam | |
| 2013/0261536 A1 | 10/2013 | Sartor | |
| 2014/0200506 A1 * | 7/2014 | Zemel | A61B 18/042 604/23 |
| 2014/0228833 A1 | 8/2014 | Friedrichs et al. | |

FOREIGN PATENT DOCUMENTS

| | | |
|---|---|---|
| DE | 4139029 A1 | 6/1993 |
| DE | 4326037 A1 | 2/1995 |
| DE | 9117019 U1 | 3/1995 |
| DE | 19524645 A1 | 2/1997 |
| DE | 19537897 A1 | 3/1997 |
| DE | 9117019 U1 | 3/2000 |
| DE | 19848784 A1 | 5/2000 |
| DE | 29724247 U1 | 8/2000 |
| EP | 0956827 A1 | 11/1999 |
| EP | 1595507 A2 | 11/2005 |
| EP | 2777580 A2 | 9/2014 |
| FR | 1340509 A | 10/1963 |
| JP | 61-159953 A | 7/1986 |
| JP | H11290335 A | 10/1999 |
| JP | 2010-242857 A | 10/2010 |
| JP | 2016500318 A | 1/2016 |
| SU | 1438745 A1 | 11/1988 |
| WO | 2009/080273 A1 | 7/2009 |
| WO | 2014094931 A1 | 6/2014 |

OTHER PUBLICATIONS

Lieberman et al., "Capacitive Discharges", Principles of Plasma Discharges and Materials Processing, John Wiley & Son, Inc. (2005) pp. 387-460.

Moore et al., "Confined Geometry Interactions of Downstream RF-Excited Atmospheric Plasma Wires", IEEE Transactions on Plasma Science, 0093-3813, (2008) pp. 1-2.

Walsh et al., "Contrasting Characteristics of Pulsed and Sinusoidal Cold Atmospheric Plasma Jets", Applied Physics Letters, 88, 171501 (2006) pp. 1-3.

Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.

Xu et al., "DBD Plasma Jet in Atmospheric Pressure Argon", IEEE Transactions on Plasma Science, vol. 36, No. 4, (Aug. 2008), pp. 1352-1353.

Alfred Grill, "Electron Cyclotron Resonance Plasmas", Cold Plasma in Materials Fabrication, IEEE Press (1994) pp. 40-43.

Brand et al., "Electrosurgical Debulking of Ovarian Cancer: A New Technique Using the Argon Beam Coagulator"; Gynecologic Oncology 39 pp. 115-118 (1990).

Grund et al., "Endoscopic Argon Plasma . . . Flexible Endoscopy"; Endoscopic Surgery and Allied Technologies, No. 1, vol. 2, pp. 42-46 (Feb. 1994).

Waye et al., "Endoscopic Treatment Options"; Techniques in Therapeutic Endoscopy, pp. 1.7-1.15, (1987).

B.D. Cullity, "Introduction to Magnetic Materials", University of Notre Dame; Addison-Wesley Publishing Company, Reading MA., (1972) pp. 23-28.

Brian Chapman, "Matching Networks", Glow Discharge Processes, John Wiley & Sons Inc., NY, (1980) pp. 153-172.

(56) References Cited

OTHER PUBLICATIONS

Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.

Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
Sobolewski, Mark A., "Current and Voltage Measurements in the Gaseous Electronics Conference RF Reference Cell". J. Res. Natl. Inst. Stand. Technol. 100, 341; Apr. 1995.
Hernandez et al., "A Controlled Study of the Argon Beam Coagultor for Partial Nephrectomy"; The Journal of Urology, vol. 143, May (1990) J. Urol. 143: pp. 1062-1065.
Partial European Search Report from Application No. EP 14158043.1 dated Jun. 10, 2014.
European Search Report dated Feb. 12, 2018 issued in EP Appln. No. 17184185.

* cited by examiner

SYSTEM AND METHOD FOR CATHETER-BASED PLASMA COAGULATION

CROSS REFERENCE TO RELATED APPLICATION

The present application claims the benefit of and priority to U.S. Provisional Application Ser. No. 62/370,035, filed on Aug. 2, 2016, the entire contents of which are incorporated herein by reference.

BACKGROUND

Technical Field

The present disclosure relates to plasma devices and systems for surface processing and tissue treatment. More particularly, the disclosure relates to a monopolar coagulation handpiece for generating chemically reactive, plasma-generated species.

Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring the plasma electron temperature and the electron density. In addition, adjusting spatial, temporal, and temperature properties of the plasma creates specific changes to the material being irradiated by the plasma species and associated photon fluxes. Plasmas are also capable of generating photons that have sufficient energy to initiate photochemical and photocatalytic reaction paths in biological and other materials that are irradiated by the plasma photons.

Although plasma-based devices to treat tissue are known, conventional plasma-based devices are not well suited for accurately controlling the effects on tissue, such as desiccation depth. This is of particular importance in surgical procedures where controlling the depth of the plasma penetration is key to achieving a desired therapeutic effect, such as in plasma treatment of ulcerative colitis, which is a disease of the inner lining (mucosa) of the colon. Ulcerative colitis is characterized by inflammation of the mucosa layer, which causes the formation of ulcers. This can in turn, cause protrusion of the colon walls into digestive pathways and may become cancerous if left untreated. Thus, the goal of plasma-based ulcerative colitis treatments is to treat the mucosa without damaging the underlying muscle layers. Accordingly, there is a need for a plasma treatment system and apparatus for generating plasma effluent that is capable of treating tissue to a desired depth.

SUMMARY

Plasmas have broad applicability and provide alternative solutions to industrial, scientific and medical needs, especially workpiece (e.g, tissue) surface treatment at any temperature range. Plasmas may be delivered to the workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece with little or no effect on a separate underlayer of the workpiece or it may be used to selectively remove a particular tissue from a mixed tissue region or selectively remove a tissue with minimal effect to adjacent organs of different tissue type.

The plasma species are capable of modifying the chemical nature of tissue surfaces by breaking chemical bonds, substituting or replacing surface-terminating species (e.g., surface functionalization) through volatilization, gasification, or dissolution of surface materials (e.g., etching). With proper techniques, material choices, and conditions, one can remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type.

According to one embodiment of the present disclosure, a plasma instrument is disclosed. The plasma instrument includes an elongated body defining a lumen therethrough, the lumen being in fluid communication with an ionizable media source; and a plasma applicator coupled to a distal portion of the elongated body. The plasma applicator includes: an active electrode configured to couple to an active terminal of a generator; and a corona electrode configured to couple to a return terminal of a generator. The plasma instrument also includes a switching element coupled to the corona electrode, the switching element configured to control at least one of resistivity or connectivity of the corona electrode to a generator.

According to one aspect of the above embodiment, the plasma instrument further includes a proximity sensor configured to measure a distance between the plasma applicator and tissue.

According to one aspect of the above embodiment, the plasma instrument further includes an atmospheric sensor configured to measure a property of air surrounding the plasma applicator.

According to one aspect of the above embodiment, the plasma applicator further includes a nozzle coupled to a distal portion of the corona electrode.

According to one aspect of the above embodiment, the active electrode extends through the corona electrode and at least partially through the nozzle.

According to one aspect of the above embodiment, the elongated body is flexible.

According to another embodiment of the present disclosure, a plasma system is disclosed. The plasma system includes: a generator having an active terminal and a return terminal; an ionizable media source; and a plasma instrument, which includes an elongated body defining a lumen therethrough, the lumen being in fluid communication with the ionizable media source; and a plasma applicator coupled to a distal portion of the elongated body. The plasma applicator includes: an active electrode coupled to the active terminal of the generator; and a corona electrode coupled to the return terminal of the generator. The plasma instrument also includes a switching element coupled to the corona electrode, the switching element configured to control at least one of resistivity or connectivity of the corona electrode to the generator.

According to one aspect of the above embodiment, the plasma system further includes a return electrode pad coupled to the return terminal.

According to one aspect of the above embodiment, the plasma system further includes a first return lead coupled to the corona electrode; a second return lead coupled to the return electrode pad; and a common return lead coupled to the first and second return leads, the common return lead being coupled to the return terminal.

According to one aspect of the above embodiment, the plasma instrument further includes a proximity sensor configured to measure a distance between the plasma applicator and tissue.

According to one aspect of the above embodiment, the generator includes a controller coupled to the proximity sensor, the controller configured to control at least one of energy output of the generator or a state of the switching element based on the distance.

According to one aspect of the above embodiment, the plasma instrument further includes an atmospheric sensor configured to measure an air property surrounding the plasma applicator.

According to one aspect of the above embodiment, the generator includes a controller coupled to the atmospheric sensor, the controller configured to control at least one of energy output of the generator or a state of the switching element based on the air property.

According to one aspect of the above embodiment, the air property is selected from the group consisting of humidity and oxygen saturation.

According to one aspect of the above embodiment, the plasma applicator further includes a nozzle coupled to a distal portion of the corona electrode. The active electrode extends through the corona electrode and at least partially through the nozzle.

According to one aspect of the above embodiment, the elongated body is flexible.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas may be generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuits that are used to deliver electrical energy to the workpiece affect many properties of the plasma. The performance of the plasma chemical generation, the delivery system and the design of the electrical excitation circuitry are interrelated. Specifically, the choices of operating voltage, frequency, and current levels (as well as phase) affect the electron temperature and electron density. Further, choices of electrical excitation and plasma device hardware also determine how a given plasma system responds dynamically to the introduction of new ingredients to the host plasma gas or liquid media.

Plasma effluent may be used to coagulate, cauterize, or otherwise treat tissue through direct application of high-energy plasma. In particular, kinetic energy transfer from the plasma to the tissue causes healing, and thus, provides for thermal coagulation of bleeding tissue. Plasma beam coagulation utilizes a handheld electrosurgical instrument having one or more electrodes that are energizable by an electrosurgical generator, which outputs a high-intensity electric field suitable for forming plasma using ionizable media (e.g., inert gas).

Briefly, the present disclosure provides an electrosurgical system including a generator configured to generate energy that is transmitted to a plasma instrument, which is also coupled to a source of an ionizable medium. The excitation waveform generated by the generator ignites the ionizable medium flowing through the plasma device, thereby forming a plasma effluent. The electrosurgical system according to the present disclosure includes various sensors, such as an atmospheric sensor and a proximity sensor, which provide measurement signals used by the generator for igniting and maintaining the plasma effluent. In addition, the plasma instrument also includes a corona electrode that aides in ignition and formation of the plasma effluent.

Figure 1:
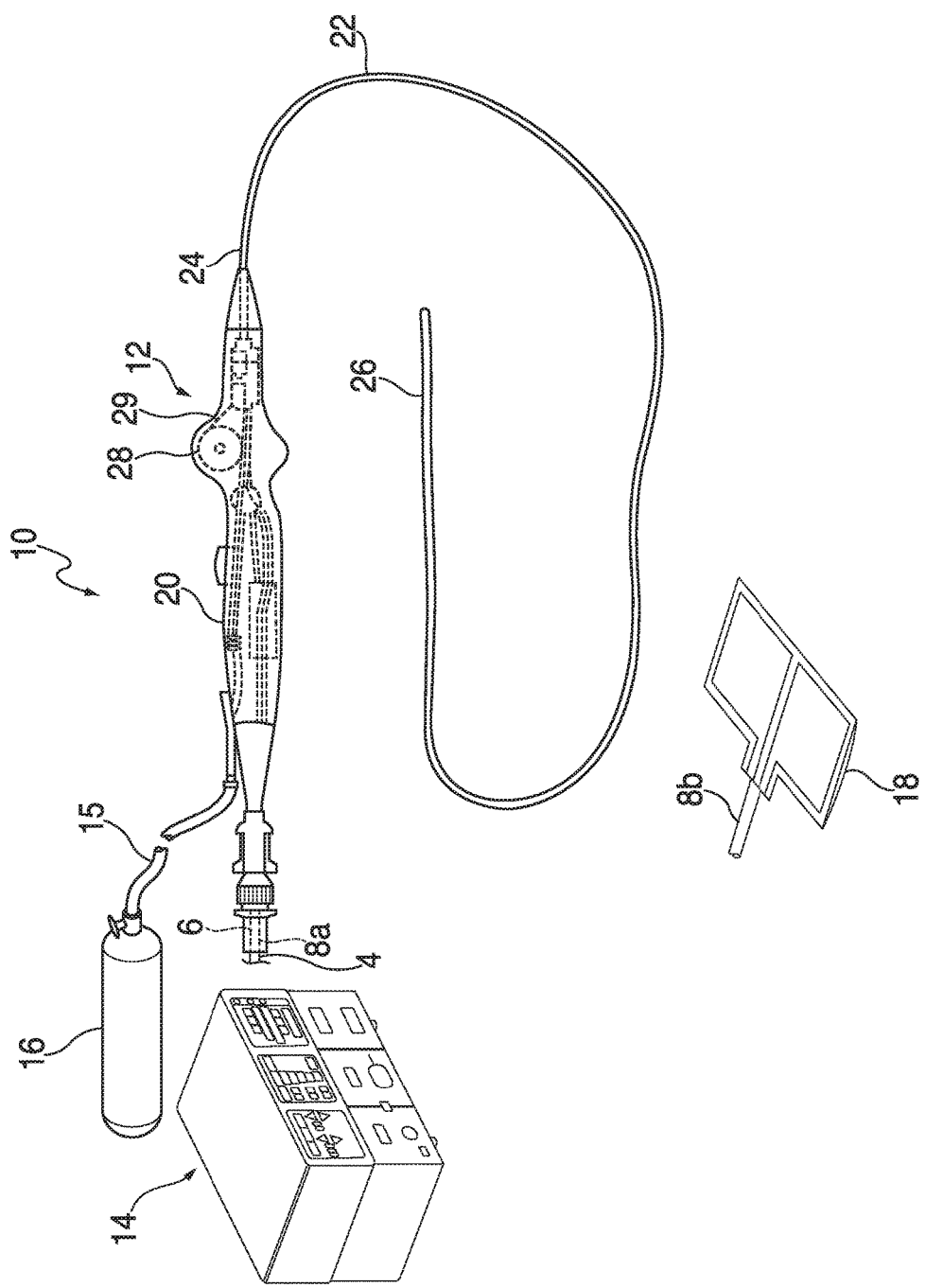
FIG. 1 is a diagram of a plasma system according to the present disclosure.

Referring initially to FIG. 1, a plasma system 10 is disclosed. The system 10 includes a plasma instrument 12 that is coupled to a generator 14, an ionizable media source 16 which may also include an optional precursor source (not shown). Generator 14 includes any suitable components for delivering power to the plasma instrument 12. More particularly, the generator 14 may be any radio frequency generator or other suitable power source capable of generating electrical power sufficient to ignite the ionizable media to generate plasma. Generator 14 may be an electrosurgical generator that is adapted to supply the instrument 12 with electrical power at a frequency from about 100 kHz to about 4 MHz, in embodiments the frequency may range from about 200 kHz to about 3 MHz, and in further embodiments the frequency may range from about 300 kHz to about 1 MHz.

In embodiments, electrosurgical energy is supplied to the instrument 12 by the generator 14 via an instrument cable 4. The cable 4 includes a supply lead 6 connecting the instrument 12 to an active terminal 230 (FIG. 5) of the generator 14 and a first return lead 8a connecting the instrument 12 to a return terminal 232 (FIG. 5) of the generator 14. It is envisioned that the plasma instrument 12 may be utilized as an electrosurgical pencil for application of plasma to tissue.

Figure 5:
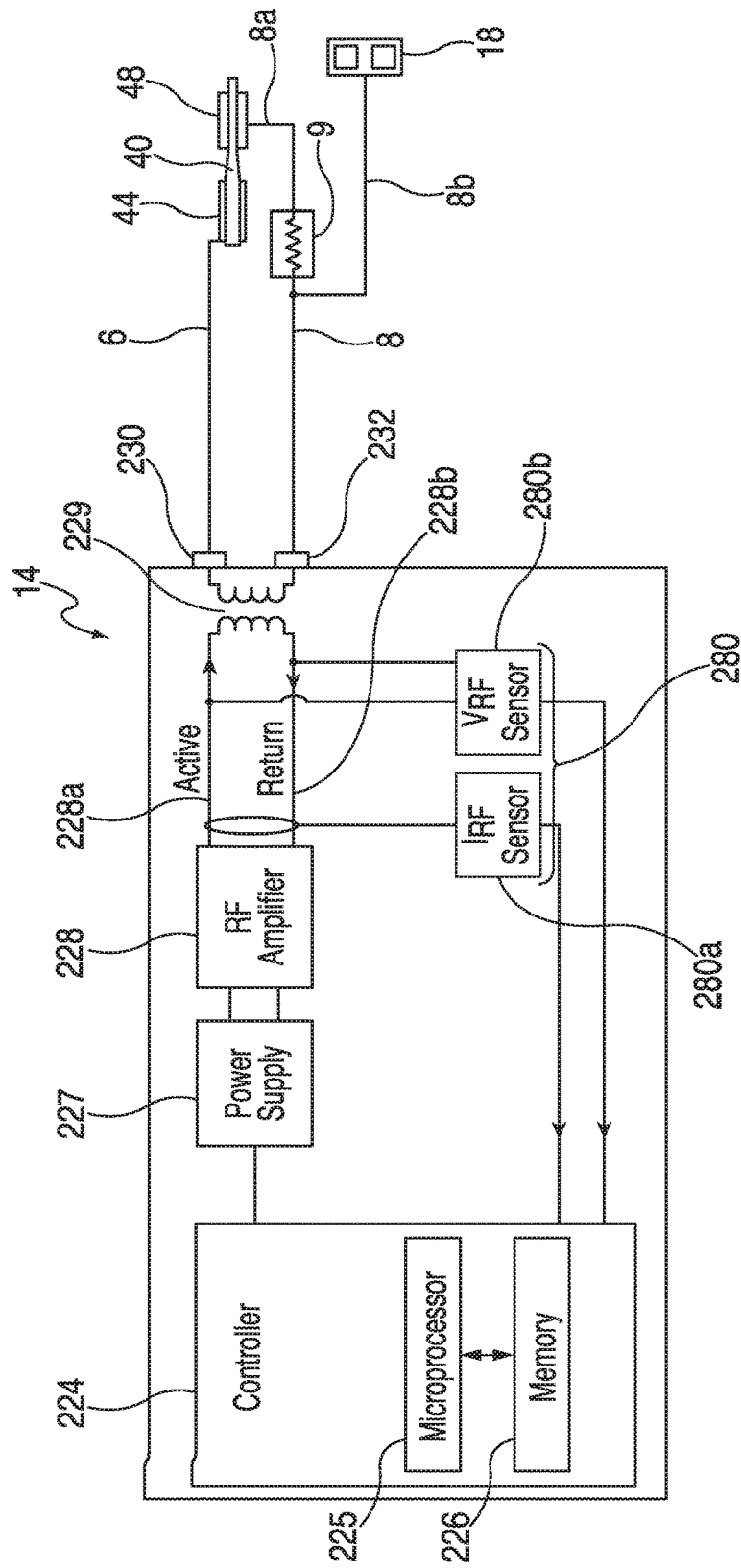
FIG. 5 is a schematic, block diagram of the plasma system of FIG. 1 according to the present disclosure.

The system 10 also includes one or more return electrode pads 18 that, in use, are disposed on a patient to minimize the chances of tissue damage by maximizing the overall contact area with the patient. The energy is returned to the generator 14 through the return electrode pad 18 via a second return lead 8b to the return terminal 232 (FIG. 5) of the generator 14. Return leads 8a and 8b are coupled to a common return lead 8, which is in turn, connected to the return terminal 232 (FIG. 5).

The plasma instrument 12 is shown as a catheter having a handle 20 and a flexible elongate body 22 having a proximal portion 24 coupled to the handle 20 and a distal portion 26. The elongate body 20 may be tubular and may be formed from any suitable flexible dielectric material, such as polyimide. The handle 20 also includes an articulation mechanism 28 having a wire 29, which extends the length of the elongate body 20. The wire 29 may be wound or unwound by the articulation mechanism 26 to articulate the distal portion 26 of the elongate body 20.

With continued reference to FIG. 1, the ionizable media source 16 may be coupled to the plasma instrument 12 via tubing 15. The tubing 15 may be fed from multiple sources of ionizable media and/or precursor feedstocks, which may be combined into unified tubing to deliver a mixture of the ionizable media and the precursor feedstock to the instrument 12 at a proximal end thereof. This allows for the plasma feedstocks, e.g., the precursor feedstock and the ionizable gas, to be delivered to the plasma instrument 12 simultaneously prior to ignition of the mixture therein.

The ionizable media source 16 may include various flow sensors and controllers (e.g., valves, mass flow controllers, etc.) to control the flow of ionizable media to the instrument 12. During operation, the ionizable media and/or the precursor feedstock are provided to the plasma instrument 12 where the plasma feedstocks are ignited to form plasma effluent containing ions, radicals, and/or photons from the specific excited species and metastables that carry internal energy to drive desired chemical reactions in the workpiece or at the surface thereof. The feedstocks may be mixed upstream from the ignition point or midstream (e.g., at the ignition point) of the plasma effluent.

The ionizable media source 16 may include a storage tank, a pump, and/or flow meter (not explicitly shown). The ionizable media may be a liquid or a gas such as argon, helium, neon, krypton, xenon, radon, carbon dioxide, nitrogen, hydrogen, oxygen, etc. their mixtures, and the like. These and other gases may be initially in a liquid form that is gasified during application. The precursor feedstock may be either in solid, gaseous or liquid form and may be mixed with the ionizable media in any state, such as solid, liquid (e.g., particulates or droplets), gas, and combinations thereof.

In another embodiment, the ionizable media and precursor feedstocks may be supplied at separate connections, such that the mixing of the feedstocks occurs within the plasma instrument 12 upstream from the ignition point. In this manner, the plasma feedstocks are mixed proximally of the ignition point.

In a further embodiment, the plasma feedstocks may be mixed midstream, e.g., at the ignition point or downstream of the plasma effluent, directly into the plasma. It is also envisioned that the ionizable media may be supplied to the instrument 12 proximally of the ignition point, while the precursor feedstocks are mixed therewith at the ignition point. In a further illustrative embodiment, the ionizable media may be ignited in an unmixed state and the precursors may be mixed directly into the ignited plasma. Prior to mixing, the plasma feedstocks may be ignited individually. The plasma feedstock may be supplied at a predetermined pressure to create a flow of the medium through the instrument 12, which aids in the reaction of the plasma feedstocks and produces a plasma effluent. The plasma according to the present disclosure may be generated at or near atmospheric pressure under normal atmospheric conditions.

In one embodiment, the precursors may be any chemical species capable of forming reactive species such as ions, electrons, excited-state (e.g., metastable) species, molecular fragments (e.g., radicals), and the like, when ignited by electrical energy from the generator 14 or when undergoing collisions with particles (electrons, photons, or other energy-bearing species of limited and selective chemical reactivity) formed from the ionizable media 16. More specifically, the precursors may include various reactive functional groups, such as acyl halide, alcohol, aldehyde, alkane, alkene, amide, amine, butyl, carboxylic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combinations thereof. In embodiments, the precursor feedstocks may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such precursor feedstocks may be applied in substantially pure, mixed, or soluble form.

Figure 2:
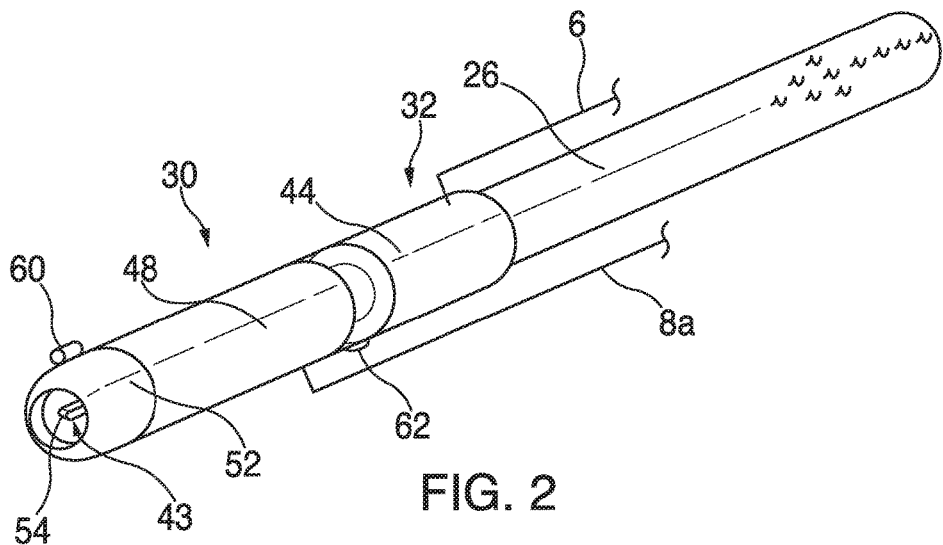
FIG. 2 is a perspective view of a plasma instrument of the system of FIG. 1.
Figure 3:
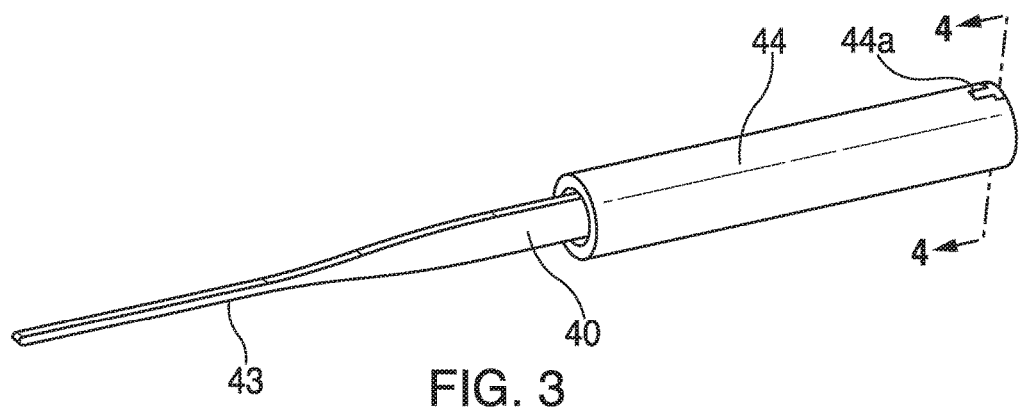
FIG. 3 is a perspective view of an electrode assembly of the plasma instrument of FIG. 2.
Figure 4:
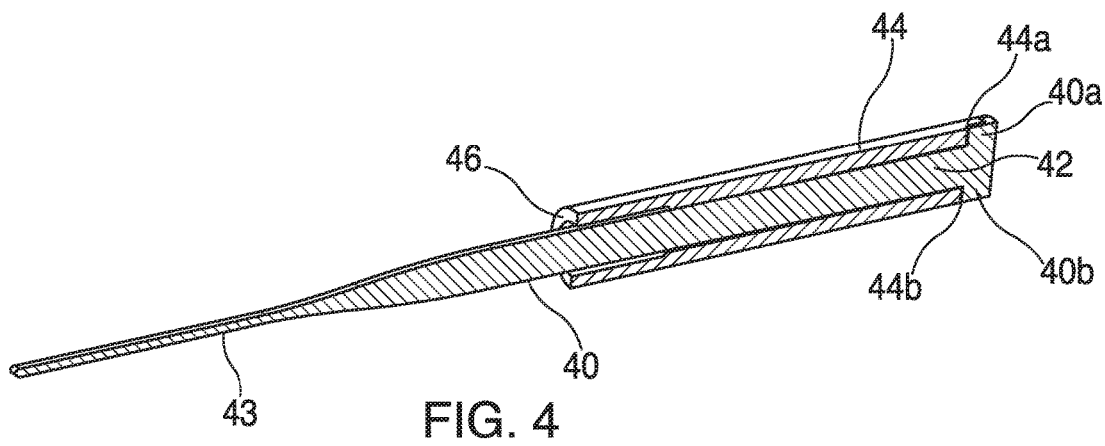
FIG. 4 is a perspective, cross-sectional view of the electrode assembly of FIG. 4 taken along a cross-sectional line 4-4.

With reference to FIG. 2-4, the distal portion 26 of the elongate body 20 is coupled to a plasma applicator 30, which includes an active electrode assembly 32. The active electrode assembly 32 includes an active electrode 40 (FIG. 3) having a proximal portion 42 and a distal portion 43 (FIG. 4). The proximal portion 42 is enclosed in a conductive collar 44, which is coupled to the supply lead 6. The supply lead 6 is electrically coupled to an outer surface of the conductive collar 44 such that the supply lead 6 is disposed outside the gas flow within the elongate body 20. In embodiments, the supply lead 6 may be enclosed in an insulative sheath and be disposed within the elongate body 20. In further embodiments, the supply lead 6 may be disposed within the tubing of the elongate body 20, e.g., during the extrusion process. In yet another embodiment, the supply lead 6 may be coupled directly to the active electrode 40.

The conductive collar 44 has a substantially tubular shape defining a lumen 46 (FIG. 4) therethrough. The distal portion 26 of the elongate body 20 may be stretched over a distal portion of the conductive collar 44 to create a gas tight seal. The conductive collar 44 may also include one or more slots 44a and 44b configured to couple to extensions 40a and 40b of the active electrode 40 to provide for an electrical and mechanical coupling therebetween. This connection also aligns the active electrode 40 within the conductive collar 44.

The active electrode 40 may have any suitable shape that does not obstruct the lumen 46, ensuring that ionizable medium may flow through the lumen 46. In embodiments, the active electrode 40 may have a tapered configuration in which the proximal portion 42 is wider than the distal portion 43 such that the change in width of the active electrode 40 is gradual from the proximal portion 42 to the distal portion 43.

The distal portion 43 of the active electrode 40 is enclosed in a corona electrode 48, which is coupled to the return lead 8a. The return lead 8a may be coupled to the corona electrode 48 (FIG. 2) in any suitable manner as described above with respect to coupling the supply lead 6 to the conductive collar 44. Similarly to the conductive collar 44, the corona electrode 48 may also have a substantially tubular shape defining a lumen (not shown) therethrough. The plasma applicator 30 also includes a nozzle 52 coupled to a distal end of corona electrode 48. The nozzle 52 also defines a lumen 54, in which the distal portion 43 of the active electrode 40 is disposed.

The active electrode 40, the conductive collar 44, and the corona electrode 48 may be formed from any suitable conductive material including metals, such as stainless steel, copper, aluminium, tungsten, and combinations and alloys thereof. The nozzle 52 may be formed from any suitable dielectric material including thermoplastic materials if the temperature of the plasma is sufficiently low or any other suitable heat-resistant dielectric material, including ceramic materials.

In embodiments, the plasma applicator 30 may also include a proximity sensor 60 (FIG. 2). The proximity sensor 60 is used to measure the distance between the tissue and the nozzle 52. The measured distance is used by the generator 14 to control energy and thereby maintain the plasma. The proximity sensor 60 may be an electromagnetic sensor configured to emit an electromagnetic field or a beam of electromagnetic radiation (e.g., visible light, infrared, etc.), and measure changes in the field or beam. In embodiments, the proximity sensor 60 may be a capacitive sensor configured to detect distance to tissue based on the dielectric properties thereof.

The plasma applicator 30 may also include an atmospheric sensor 62, such as a humistor, configured to sense relative humidity in and around the surgical site. In embodiments, the atmospheric sensor 62 may be also include an oxygen sensor configured to measure concentration of oxygen in the surrounding atmosphere.

FIG. 5 shows a schematic block diagram of the generator 14 configured to output electrosurgical energy. The generator 14 includes a controller 224, a power supply 227, and a radio-frequency (RF) amplifier 228. The power supply 227 may be a high voltage, DC power supply connected to an AC source (e.g., line voltage), provides high voltage, DC power to the RF amplifier 228, which then converts the high voltage, DC power into AC energy (e.g., electrosurgical or microwave) suitable to ignite the ionizable media, and delivers the energy to the active terminal 230. The energy is returned thereto via the return terminal 232. The active and return terminals 230 and 232 are coupled to the RF amplifier 228 through an isolation transformer 229. The RF amplifier 228 is configured to operate in a plurality of modes, during which the generator 14 outputs corresponding waveforms having specific duty cycles, peak voltages, crest factors, etc. It is envisioned that in other embodiments, the generator 14 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 14 according to either open and/or closed control loop schemes. A closed loop control scheme is a feedback control loop, in which a plurality of sensors measure a variety of tissue and energy properties (e.g., tissue impedance, tissue temperature, output power, current, and/or voltage, etc.), and provide feedback to the controller 224. The controller 224 then signals the power supply 227 and/or RF amplifier 228, which adjusts the DC and/or power supply, respectively. Those skilled in the art will appreciate that the processor 225 may be substituted by using any logic processor (e.g., control circuit) adapted to perform the calculations and/or set of instructions described herein including, but not limited to, field programmable gate array, digital signal processor, and combinations thereof.

The generator 14 according to the present disclosure includes a plurality of sensors 280, e.g., an RF current sensor 280*a*, and an RF voltage sensor 280*b*. Various components of the generator 14, namely, the RF amplifier 228, and the RF current and voltage sensors 280*a* and 280*b*, may be disposed on a printed circuit board (PCB). The RF current sensor 280*a* is coupled to the active terminal 230 and provides measurements of the RF current supplied by the RF amplifier 228. In embodiments the RF current sensor 280*a* may be coupled to the return terminal 232. The RF voltage sensor 280*b* is coupled to the active and return terminals 230 and 232 provides measurements of the RF voltage supplied by the RF amplifier 228. In embodiments, the RF current and voltage sensors 280*a* and 280*b* may be coupled to active and return leads 228*a* and 228*b*, which interconnect the active and return terminals 230 and 232 to the RF amplifier 228, respectively.

The RF current and voltage sensors 280*a* and 280*b* provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 14 and/or the plasma instrument 12. The controller 224 utilizes the input signals to adjust the power output of the generator 14 and/or performs other control functions thereon.

The controller 224 is also coupled to the proximity sensor 60 and the atmospheric sensor 62 (FIG. 2). The controller 224 operates the generator 14 based on the sensor signals from the proximity sensor 60 and the atmospheric sensor 62. In embodiments, the controller 224 may also be configured to control the ionizable media source 16 (FIG. 1), such as the flow rate of the ionizable media, based on the sensor readings.

With continued reference to FIG. 5, the controller 224 is also configured to control the output of the generator 14 to ensure proper ignition of the plasma effluent. In that respect, the generator 14 includes a switching element 9 coupled to the first return lead 8*a*. The switching element 9 controls the degree of coupling of the corona electrode 48 to the generator 14.

The switching element 9 may be a resistor, a variable resistor, a switch or combinations of these components. In embodiments, the switching element 9 may be coupled to the return lead 8 in parallel such that the switching element 9 may be switched in and out of the combined circuit. The switch state and/or the resistance of the switching element 9 may be controlled by the controller 224. The resistance provided by the switching element 9 is used to control the amount of power delivered to the corona electrode 48. In particular, where the switching element 9 is a variable resistor the resistance may be lowered to ensure that most of the power is delivered to the surgical site through the active electrode 40 and the corona electrode 48 to commence plasma generation. After the plasma has been ignited, the controller 224 may then increase resistance of the switching element 9 to a level higher than the starting level to maintain plasma.

In embodiments where the switching element 9 is a switchable resistor, to commence plasma generation the switching element 9 may be initially disconnected from the combined return lead 8 by the controller 224. Once the plasma has commenced, the switching element 9 may then be switched on to maintain plasma generation.

In another embodiment, the switching element 9 may be a switch, such that after the plasma is started, the controller 224 disconnects the corona electrode 48 by deactivating the switch. In further embodiments, the plasma applicator 30 may include a plurality of corona assemblies 48 each of which is coupled to the generator 14 by the return lead 8*a* having the switching element 9. In this configuration, the controller 224 controls each of the corona assemblies 48 in the manner described above.

In other words, when the corona electrode 48 is coupled to the common return lead 8 due to the switching element 9 being activated or the resistance of the switching element 9 being lowered, the power is split between the corona electrode 48 and the return electrode pad 18. When the corona electrode 48 is disconnected from the common return lead 8 due to the switching element 9 being deactivated or the resistance of the switching element 9 being increased, the power is returned mostly through the return electrode pad 18. With respect to the switching element 9 being a variable resistor, the effect of the corona electrode 48 on plasma generation may be varied based on a desired effect.

As noted above, the controller 224 is also coupled to the proximity sensor 60 and the atmospheric sensor 62. The sensor data from the proximity sensor 60 and the atmospheric sensor 62 is used by the controller 224 to control the plasma ignition process, and in particular, the coupling of the corona electrode 48 to the generator 14. The proximity sensor 60 provides information regarding the distance separating the plasma applicator 30 from tissue. The controller 224 utilizes the distance information from the proximity sensor 60 in determining whether energy from the generator 14 may be supplied to the plasma applicator 30 to commence treatment. If the proximity sensor 60 detects that the applicator 30 is contacting tissue, then the controller 224 prevents application of energy. In embodiments, the controller 224 is also configured to control energy output based on the measured distance, such as increasing energy as the distance between the applicator 30 and the tissue increases and decreasing energy as the distance decreases.

The atmospheric sensor 62 provides data to the controller 224 regarding the atmosphere surrounding the plasma applicator 30, the data including oxygen saturation, pressure, relative humidity, and the like. The controller 224 utilizes this data in controlling energy delivered to the plasma applicator 30. Humidity and density of the atmosphere, e.g., oxygen saturation, play an important role in the effectiveness of the plasma. Decreased oxygen saturation and increased humidity adversely affect plasma performance, and therefore, the controller 224 adjusts the output of the generator 14 such that the energy supplied by the generator 14 compensates for any adverse atmospheric effects as measured by the atmospheric sensor 62.

Figure 6:
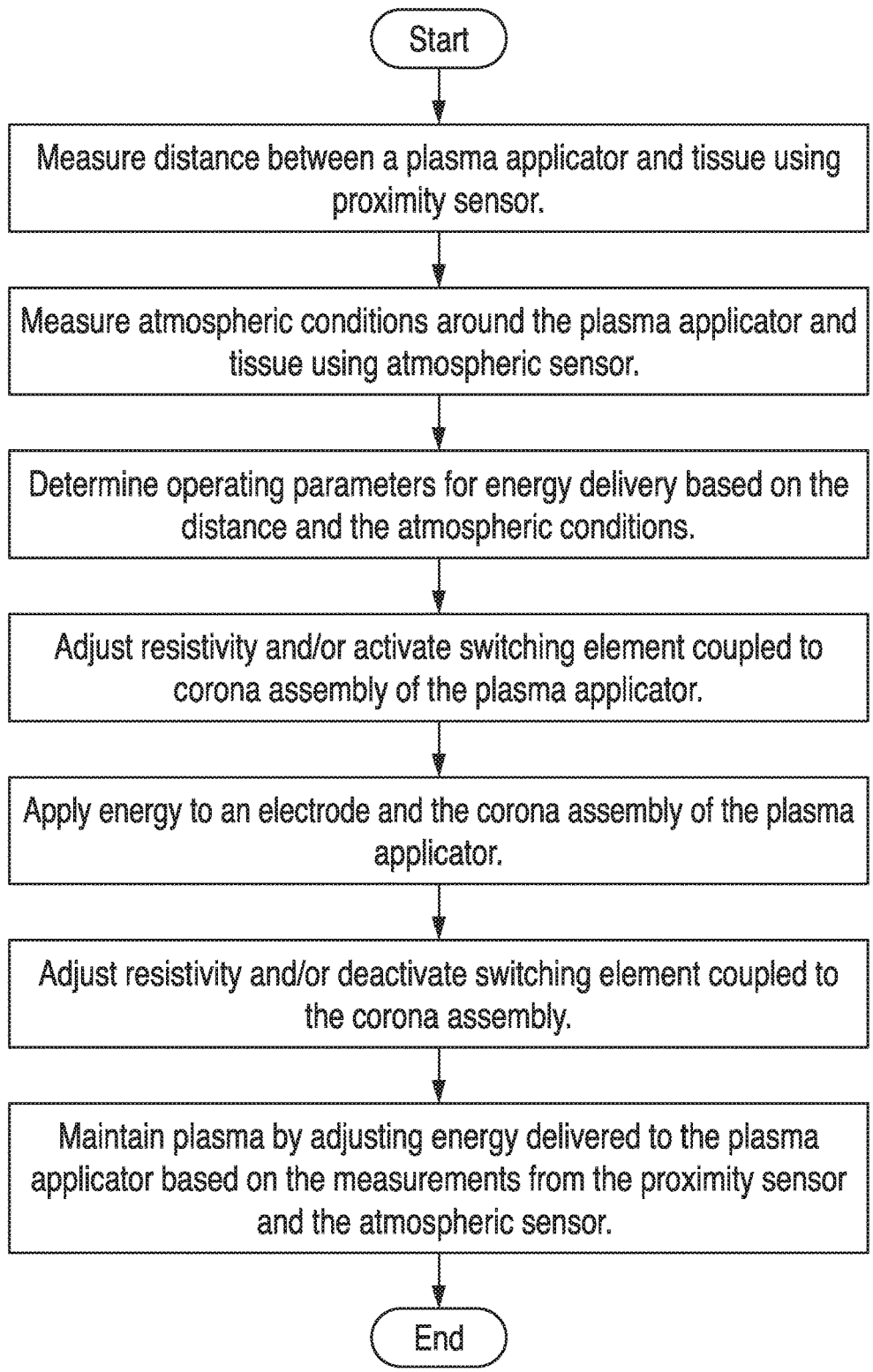
FIG. 6 is a flow chart of a method for generating plasma using the plasma system of FIG. 1.

With reference to FIG. 6, a method for operating the system 10 according to the present disclosure, initially includes measuring the distance and atmospheric conditions of the plasma applicator 30. The measurements are transmitted to the controller 224, which determines operating parameters of the generator 14 based on the measurements. If the plasma applicator 30 is detected to be contacting tissue, the controller 224 may output an error signal, indicating that the plasma applicator 30 may need to be repositioned to avoid contact. Once the controller 224 determines that the plasma applicator 30 is separated by a sufficient distance, the controller 224 adjusts resistivity of the switching element 9 and/or activates the switching element 9 depending on the configuration of the switching element 9 and the combined return lead 8. In embodiments where the corona electrode 48 is connected via a switch (not shown) instead of the switching element 9, then the switch is actuated by the controller 224.

After the distance and resistance are set and/or determined by the controller 224 to be within prescribed operating parameters, the controller 224 signals the generator 14 to output energy to ignite plasma. The controller 224 calculates the initial energy output in view of the atmospheric conditions, distance, and resistance. In embodiments where resistivity is adjustable, resistivity of the switching element 9 may also be calculated by the controller 224. Thereafter, the generator 14 outputs energy based on these calculations.

After plasma has been ignited at the plasma applicator 30, the controller 224 deactivates the switching element 9 and/or adjusts the resistivity thereof to a desired level to maintain the plasma. Additionally, the controller 224 may also utilize the measurements from the proximity sensor 60 and the atmospheric sensor 62 after the plasma has been ignited to make adjustments to the output of the generator 14.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows the tailoring of the relative populations of plasma species to meet needs for the specific process desired on the workpiece surface or in the volume of the reactive plasma.

What is claimed is:

1. A plasma instrument comprising:
   an elongated body defining a lumen therethrough, the lumen being in fluid communication with an ionizable media source;
   a plasma applicator coupled to a distal portion of the elongated body, the plasma applicator including:
   an active electrode configured to couple to an active terminal of a generator; and
   a corona electrode configured to couple to a return terminal of a generator; and
   a switching element coupled to the corona electrode, the switching element configured to switch between a first state and a second state, wherein during the first state and the second state the corona electrode is electrically coupled to a generator.

2. The plasma instrument according to claim 1, further comprising a proximity sensor configured to measure a distance between the plasma applicator and tissue.

3. The plasma instrument according to claim 1, further comprising an atmospheric sensor configured to measure a property of air surrounding the plasma applicator.

4. The plasma instrument according to claim 1, wherein the plasma applicator further includes a nozzle coupled to a distal portion of the corona electrode.

5. The plasma instrument according to claim 4, wherein the active electrode extends through the corona electrode and at least partially through the nozzle.

6. The plasma instrument according to claim 1, wherein the elongated body is flexible.

7. A plasma system comprising:
   a generator including:
   an active terminal;
   a return terminal; and a controller;
an ionizable media source;
a plasma instrument including:
   an elongated body defining a lumen therethrough, the lumen being in fluid communication with the ionizable media source;
   a plasma applicator coupled to a distal portion of the elongated body, the plasma applicator including:
     an active electrode coupled to the active terminal of the generator; and
     a corona electrode configured to couple to a return terminal of a generator; and
   a switching element coupled to the corona electrode, the switching element-configured to switch between a first state and a second state, wherein during the first state and the second state the corona electrode is electrically coupled to the generator.

8. The plasma system according to claim 7, further comprising a return electrode pad coupled to the return terminal.

9. The plasma system according to claim 8, further comprising:
   a first return lead coupled to the corona electrode;
   a second return lead coupled to the return electrode pad; and
   a common return lead coupled to the first and second return leads, the common return lead being coupled to the return terminal.

10. The plasma system according to claim 7, wherein the plasma instrument further includes a proximity sensor configured to measure a distance between the plasma applicator and tissue.

11. The plasma system according to claim 10, wherein the controller is further configured to control at least one of energy output of the generator or a state of the switching element based on the distance.

12. The plasma system according to claim 7, wherein the plasma instrument further includes an atmospheric sensor configured to measure an air property surrounding the plasma applicator.

13. The plasma system according to claim 12, wherein the controller is further configured to control at least one of energy output of the generator or a state of the switching element based on the air property.

14. The plasma system according to claim 12, wherein the air property is selected from the group consisting of humidity and oxygen saturation.

15. The plasma system according to claim 7, wherein the plasma applicator further includes a nozzle coupled to a distal portion of the corona electrode.

16. The plasma system according to claim 15, wherein the active electrode extends through the corona electrode and at least partially through the nozzle.

17. The plasma system according to claim 7, wherein the elongated body is flexible.

* * * * *